United States Patent
Cox et al.

(10) Patent No.: US 8,376,993 B2
(45) Date of Patent: Feb. 19, 2013

(54) MULTIPLE DOSAGE INJECTOR

(75) Inventors: Janice L. Cox, St. Paul, MN (US);
Matthew Rust, Hudson, WI (US);
Thomas E. KraMer, Coon Rapids, MN (US); Peter Hoeft, Lindstrom, MN (US)

(73) Assignee: Antares Pharma, Inc., Ewing, NJ (US)

( * ) Notice: Subject to any disclaimer, the term of this patent is extended or adjusted under 35 U.S.C. 154(b) by 0 days.

(21) Appl. No.: 12/536,106

(22) Filed: Aug. 5, 2009

(65) Prior Publication Data

US 2010/0036320 A1 Feb. 11, 2010

Related U.S. Application Data

(60) Provisional application No. 61/086,363, filed on Aug. 5, 2008.

(51) Int. Cl.
*A61M 5/00* (2006.01)
*A61M 5/30* (2006.01)
(52) U.S. Cl. ............................ 604/110; 604/68; 604/207
(58) Field of Classification Search .............. 604/68–72, 604/134–139, 110
See application file for complete search history.

(56) References Cited

U.S. PATENT DOCUMENTS

| | | | |
|---|---|---|---|
| 3,790,048 A | 2/1974 | Luciano et al. ............... 222/390 |
| 4,592,745 A | 6/1986 | Rex et al. ...................... 604/211 |
| 4,883,472 A | 11/1989 | Michel | |
| 5,304,152 A * | 4/1994 | Sams ........................... 604/207 |
| 5,743,889 A * | 4/1998 | Sams ........................... 604/207 |
| 6,004,297 A * | 12/1999 | Steenfeldt-Jensen et al. ............................. 604/211 |
| 6,083,201 A | 7/2000 | Skinkle ........................ 604/151 |
| 6,221,053 B1 | 4/2001 | Walters et al. ................ 604/211 |
| 6,562,006 B1 | 5/2003 | Hjertman et al. ............. 604/208 |
| 6,620,137 B2 | 9/2003 | Kirchhofer et al. | |
| 6,899,698 B2 * | 5/2005 | Sams ........................... 604/211 |
| 6,936,032 B1 | 8/2005 | Bush, Jr. et al. .............. 604/187 |
| 7,018,364 B2 | 3/2006 | Giambattista et al. | |
| 2003/0158523 A1 * | 8/2003 | Hjertman et al. ............. 604/207 |
| 2004/0097783 A1 | 5/2004 | Peters et al. .................... 600/16 |
| 2004/0097883 A1 | 5/2004 | Roe | |
| 2004/0267207 A1 * | 12/2004 | Veasey et al. ................. 604/208 |
| 2007/0088288 A1 | 4/2007 | Barron et al. ................. 604/207 |
| 2007/0123829 A1 | 5/2007 | Atterbury et al. | |
| 2009/0254027 A1 * | 10/2009 | Moller ........................... 604/71 |

OTHER PUBLICATIONS

International Search Report and Written Opinion of the International Searching Authority, application No. PCT/US2009/052835, Mar. 15, 2010.

* cited by examiner

*Primary Examiner* — Nicholas Lucchesi
*Assistant Examiner* — Jenna Zhang
(74) *Attorney, Agent, or Firm* — Morgan, Lewis & Bockius LLP

(57) ABSTRACT

A medicament dispensing mechanism is disclosed that is configured to eject successive doses of the medicament from a medicament chamber. An embodiment of the dispensing mechanism includes a housing and a plunger rod configured for ejecting the doses of medicament from the chamber. The dispensing mechanism further includes an actuation mechanism that comprises a trigger associated with the housing and having a ready and a fired position with respect thereto. The trigger is configured for manipulation by a user for successive movement in a generally axial dosing motion from the ready position to the fired position in which the trigger is associated with the plunger rod to cause the plunger rod to eject one of the doses of a predetermined volume and a resetting motion from the fired position to the ready position that comprises axial rotation, wherein the trigger is uncoupled from the plunger rod during the resetting motion.

23 Claims, 7 Drawing Sheets

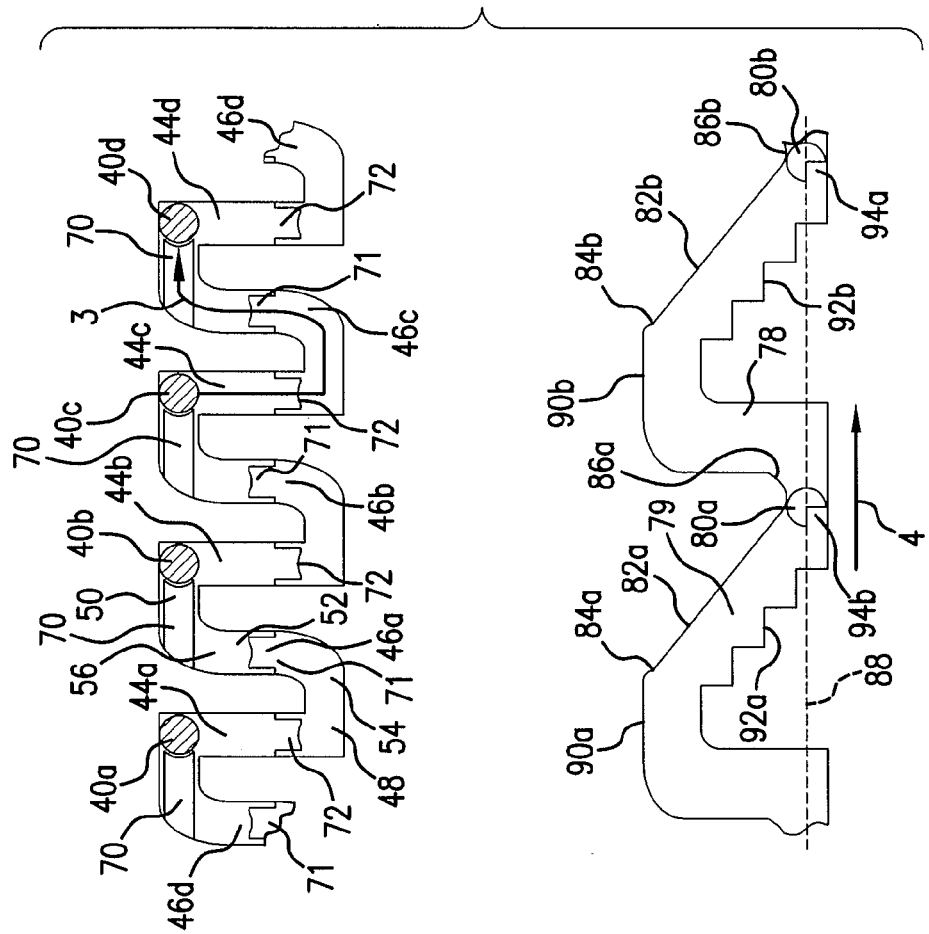
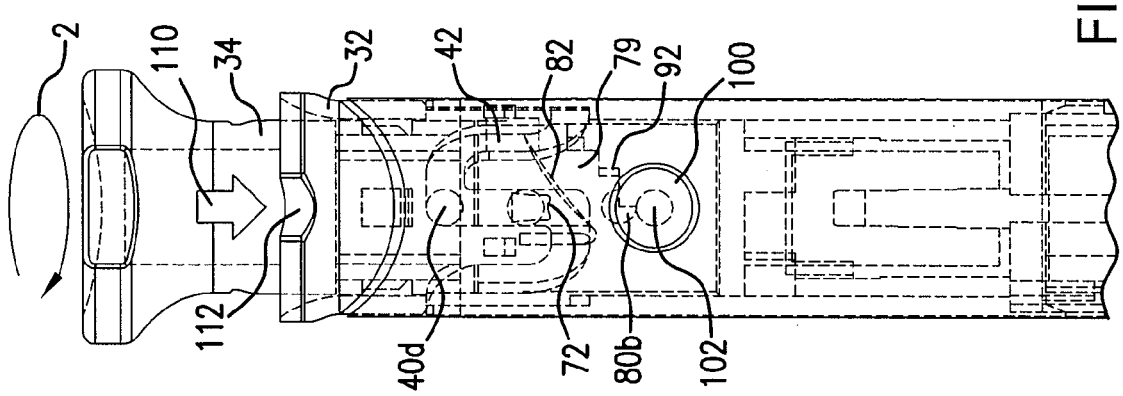
FIG. 4B
FIG. 4A

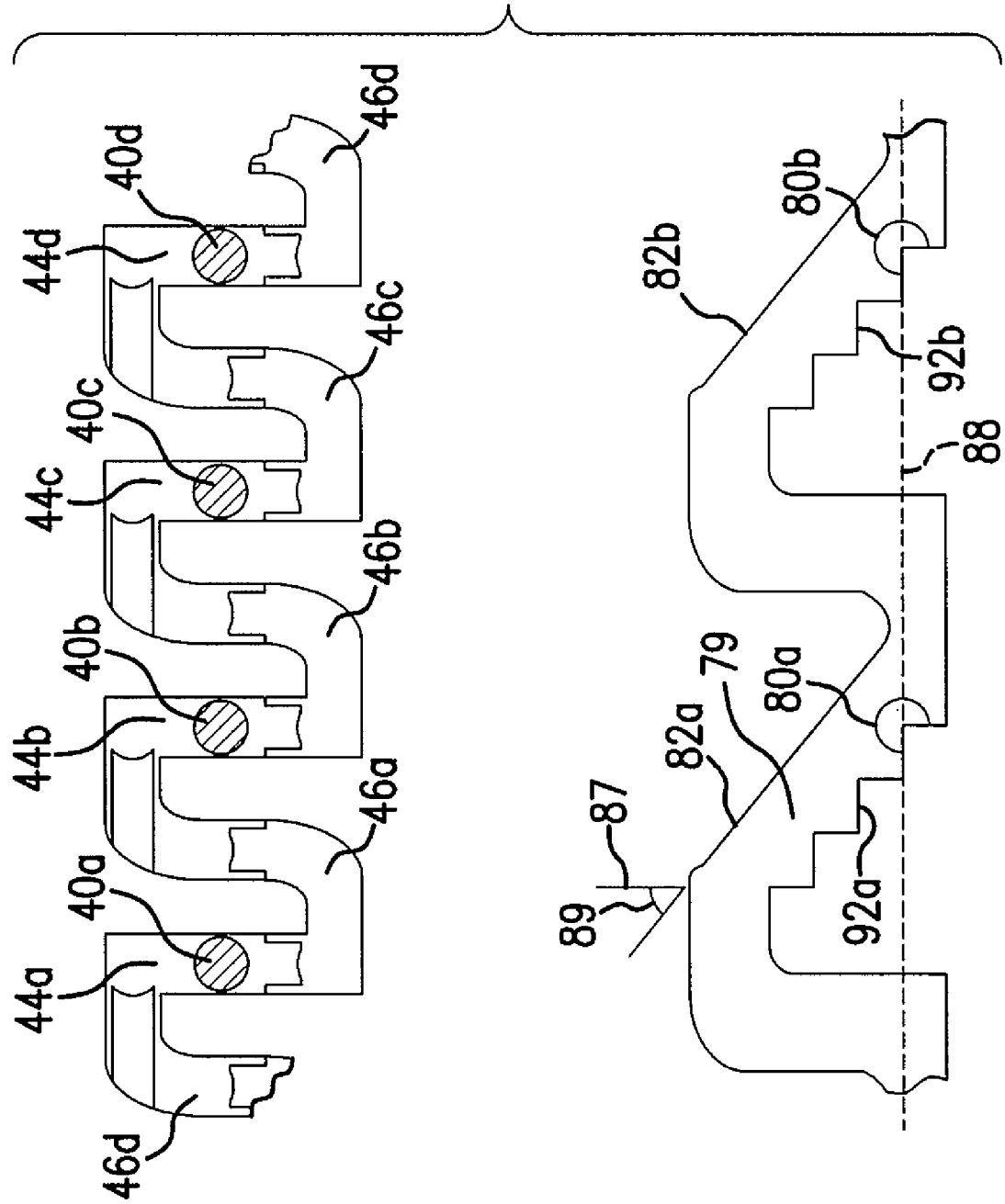

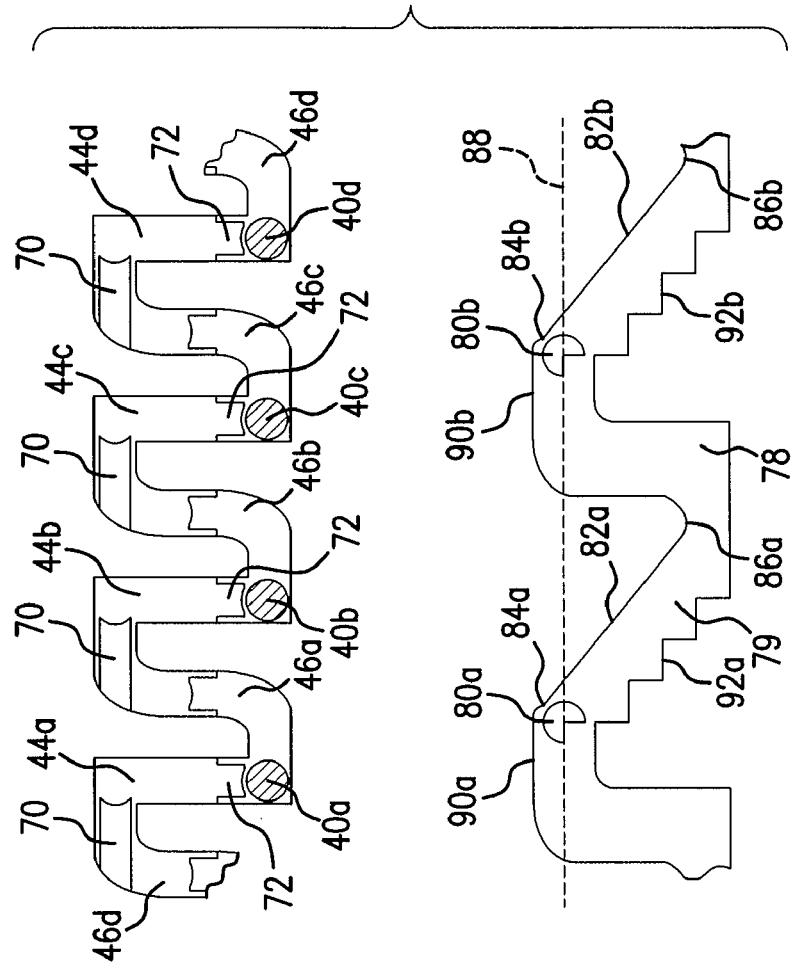
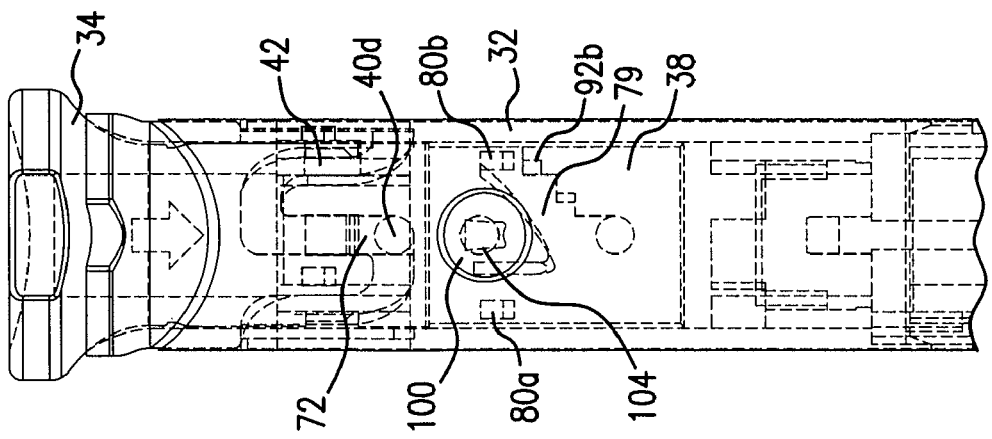

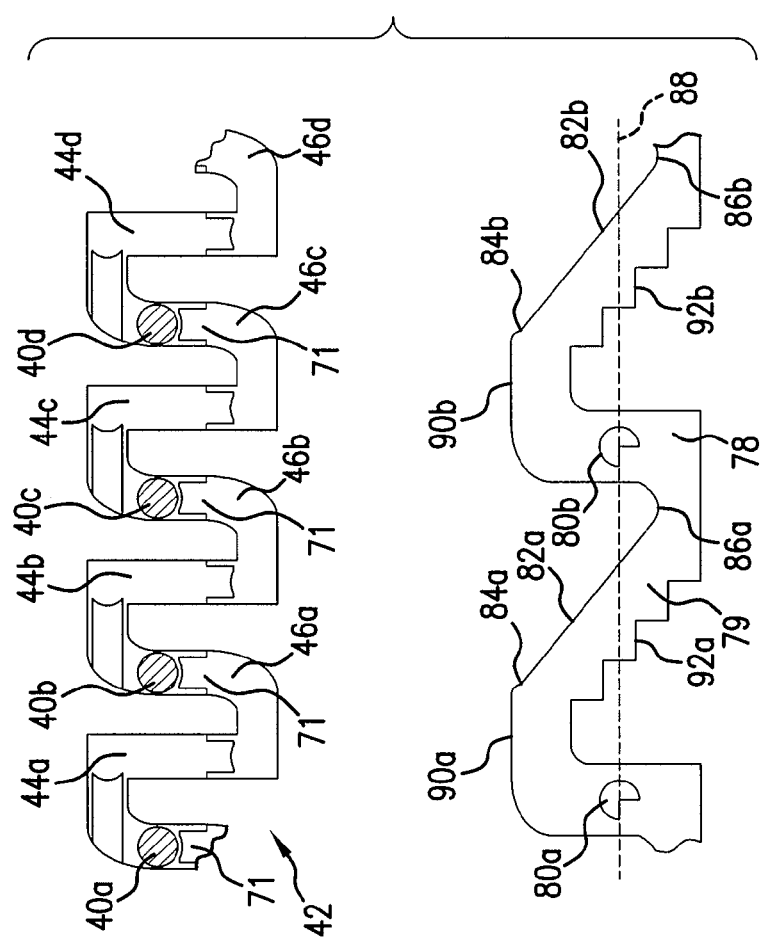
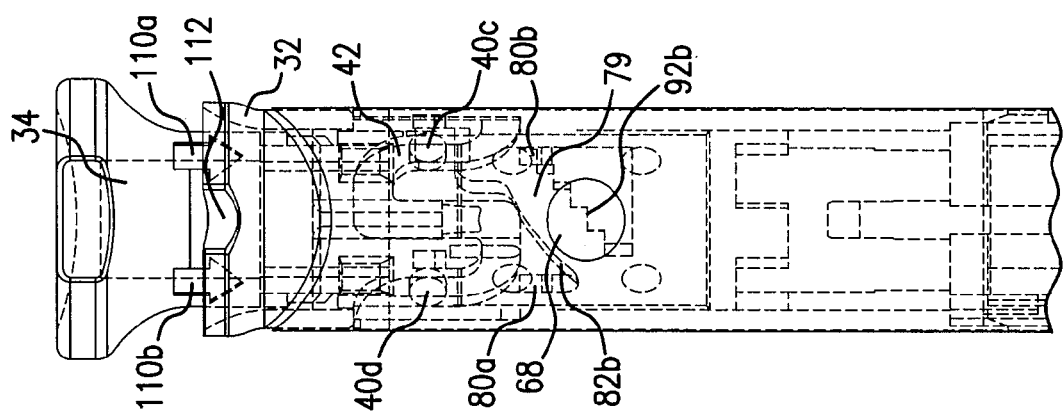
FIG. 7A
FIG. 7B

MULTIPLE DOSAGE INJECTOR

This application claims the benefit of U.S. Provisional Application No. 61/086,363 filed Aug. 5, 2008, the entire content of which is expressly incorporated herein by reference thereto.

BACKGROUND OF THE INVENTION

The present invention relates to an injection device capable of delivering multiple doses of a liquid medicament contained therein without the need to refill the device between doses.

Various types of drug treatments, including hormone therapy and the like, require administration of the drug-containing liquid medicament at regular intervals over an extended period of time. For example, a specific hormone treatment can require daily administration of the drug for a period of thirty days. In such a situation, it is advantageous to provide a device that allows the patient to self-administer the injection to avoid repeated trips to a doctor's office or the like.

Various injection devices have been developed that allow self-administration of multiple doses of medication. For example, U.S. Pat. No. 4,592,745 provides an injection device that includes a unidirectional transmission mechanism that advances a piston rod in successive axial steps based on advancing axial movement of a pressure device. Similarly, U.S. Pat. No. 3,790,048 discloses an injection device that uses a cam barrel and a ratchet to translate actuation of a trigger to cause advancement of a plunger and to cause the plunger to remain stationary during repositioning of the trigger. In both of these devices, the reciprocal motion of the trigger is such that the return stroke follows the same path as the dosing stroke, but in an opposite direction.

U.S. Pat. No. 6,562,006 discloses a device that uses rotation of the trigger to reset the device for successive dosing. Another reference describes a device that is also adjustable between a priming dose and an injection dose. The dosing of these devices is selectable by the user, which can allow errors in selecting the dose, potentially reducing the efficacy of the medication or leading to harmful side effects.

U.S. Patent Application Pub. No. 2007/0088288 describes a device that allows a user to administer a fixed dose of the liquid medicament contained therein. The device does not use a reduction mechanism, but rather has a trigger that disengages from the piston rod when depressed to give the user a feeling of a longer trigger motion.

A device is needed that allows for repeated administration of a dose of medicament that is easy to use correctly in self-administration.

SUMMARY OF THE INVENTION

An aspect of the present invention relates to a medicament dispensing mechanism configured to eject successive doses of the medicament from a medicament chamber. An embodiment of the dispensing mechanism includes a housing and a plunger rod configured for ejecting the doses of medicament from the chamber. The dispensing mechanism further includes an actuation mechanism that comprises a trigger associated with the housing and having a ready and a fired position with respect thereto. The trigger is configured for manipulation by a user for successive movement in a dosing motion from the ready position to the fired position generally in axial translation in which the trigger is associated with the plunger rod to cause the plunger rod to eject one of the doses of a predetermined volume and a resetting motion from the fired position to the ready position that comprises axial rotation, wherein the trigger is uncoupled from the plunger rod during the resetting motion. In a preferred embodiment, the volume of the doses is preset and fixed.

In a preferred embodiment, the trigger comprises a plurality of ready positions and fired positions disposed in sequence with each other, the ready positions preferably being circumferentially spaced about the housing.

A further embodiment of the device preferably includes an anti-retrograde mechanism associated with the actuation mechanism for preventing rearward movement thereof against the direction of operation of the actuation mechanism through at least a portion of the dosing and resetting motions. The anti-retrograde mechanism can be associated with the trigger for preventing rearward movement thereof from the ready position against the direction of the resetting motion. Additionally or alternatively, the anti-retrograde mechanism can be associated with the trigger for preventing rearward movement thereof from the fired position against the direction of the dosing motion.

The actuation mechanism can comprise a driver rotatably associated with the housing and driven to rotate in a driving direction by the trigger during the dosing motion. In an embodiment, the driving direction is in an opposite rotational direction than the rotational spacing between the fired position and adjacent ready position of the trigger, the driver being associated with the plunger rod for causing the plunger rod to eject said one of the doses.

The dispensing mechanism can be included in an injector that further comprises a cartridge associated with the housing and defining the chamber, a plunger disposed in the chamber to seal the medicament therein, wherein the plunger rod is associated with the plunger for forcing the plunger in a distal direction for ejecting the doses, and a needle in fluid communication with the chamber for injecting the doses into a patient.

Another aspect of the present invention relates to medicament dispensing mechanism configured to eject successive doses of the medicament from a medicament chamber. The dispensing mechanism includes a housing, and a plunger rod configured for ejecting the doses of medicament from the chamber. The dispensing mechanism further includes an actuation mechanism that comprises a trigger associated with the housing and having a ready and a fired position with respect thereto. The trigger is configured for manipulation by a user for successive movement in a dosing motion from the ready position to the fired position, during the dosing motion the trigger being associated with the plunger rod to cause the plunger rod to eject one of the doses and a resetting motion from the fired position to the ready position, wherein the trigger is uncoupled from the plunger rod during the resetting motion. The dispensing mechanism further includes an anti-retrograde mechanism associated with the actuation mechanism for preventing rearward movement thereof against the direction of operation of the actuation mechanism through at least a portion of the dosing and resetting motions.

In an embodiment of the dispensing mechanism, the actuation mechanism comprises a driver rotatably associated with the housing and driven to rotate by the trigger during the dosing motion. The driver is associated with the plunger rod for causing the plunger rod to eject said one of the doses, and the anti-retrograde mechanism is configured for preventing rearward movement of the driver with respect to the trigger against the dosing motion.

A further aspect relates to medicament administering device including a housing, a container portion associated with the housing and defining an medicament chamber containing a medicament and including a plunger moveably disposed within an end thereof. A needle is in fluid communication with the interior cavity and configured for injecting the medicament. The device further includes a reduction mechanism including a plunger rod in threaded association with the housing and configured to move the plunger in a proximal direction upon rotation thereof, a trigger moveable in a generally axial direction, and a driver associated with the trigger and plunger rod for rotating upon movement of the trigger in the axial direction and thereby causing the plunger rod to rotate relative to the housing for ejecting the medicament through the needle, wherein the driver includes a projection, and the trigger includes a stepped surface facing the projection for engaging the projection upon movement of the trigger in a direction opposite the axial direction to prevent rearward movement thereof.

BRIEF DESCRIPTION OF THE DRAWINGS

These and other objects, features and advantages of the invention will be apparent from a consideration of the following non-limiting detailed description considered in conjunction with the drawing figures, in which:

FIG. 4A is a side view of the proximal portion of the injection device of FIG. 1 showing internal features thereof when the injection device is in a ready position;

FIG. 4B is a two-dimensional representation of the tracks and the associated projections of the injection device as depicted in FIG. 4A;

FIG. 5 is a two-dimensional representation of the tracks and associated projections of the injection device of FIG. 1 during a state of use thereof;

FIG. 6A is a side view of the proximal portion of the injection device of FIG. 1 showing some of the internal features thereof when the injection device is in a fired position;

FIG. 6B is a two-dimensional representation of the tracks and associated projections of the injection device as depicted in FIG. 6A;

FIG. 7A is a side view of the proximal portion of the injection device of FIG. 1 showing internal features thereof when the injection device is in a resetting position;

FIG. 7B is a two-dimensional representation of the tracks and the associated projections of the injection device as depicted in FIG. 7A;

DETAILED DESCRIPTION OF THE PREFERRED EMBODIMENTS

Figure 1:
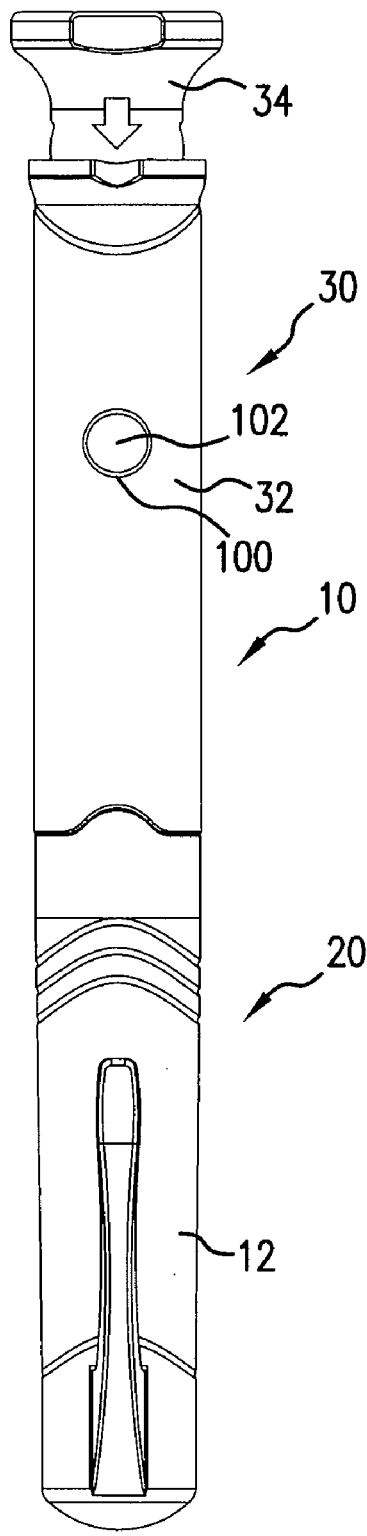
FIG. 1 is a side view of an injection device according to an embodiment of the present invention.

Referring to FIG. 1, an injector 10 of a preferred embodiment is shown having a removable cover 12 attached thereto. Injector 10 is shown in the configuration and size of a pen injector; although other known shapes and sizes are possible. Injector 10 includes a proximal section 30 and a distal section 20. Distal section includes a lower housing 22 that forms a generally cylindrical shape that is configured to hold a medicament-containing cartridge 24. Cartridge 24 can be of the type typically used in connection with injection devices, and preferably needled injector devices, and is preferably formed of glass or certain types of plastic that have qualities that are necessary for storage of liquid medicament. Such qualities include low air permeation, lubricity, low leeching of chemicals and corrosion resistance. Cartridge 24 is preferably generally cylindrical in shape and has a diameter configured to fit within lower housing 22, although other shapes can be used. Further, cartridge 24 is configured to contain a predetermined amount of a liquid medicament. The predetermined amount of liquid medicament that the cartridge is configured to contain will vary with the medicament injected and with the recommended dose size for the particular medicament and the patient.

Injector 10 is constructed to be suitable for administering repeated, successive doses of a liquid medicament. Preferably, the medicament is delivered in successive repeated fixed doses, although in some embodiments, the dosage can be controlled and adjusted. Some medicaments that can be used with the injector of the preferred embodiment include parathyroid hormone ("PTH") and various other medications such as exenatide and the like. Because of the repeated nature of the dosing of these types of medicaments, it is beneficial to use a device that aides a patient in self-administration of the doses. Further, many such medicaments should be delivered in a precise amount to ensure efficacy and to reduce side-effects.

To reliably provide repeated small doses of a liquid medicament, cartridge 24 is constructed to hold a predetermined number of doses, preferably corresponding to a predetermined period of medicament administration. For example, one embodiment of injector 10 can be intended for use with a PTH solution that is to be administered once daily for thirty successive days at a dose of 0.08 mL administered through movement of a plunger 25 through a distance of about 1.1 mm. Accordingly, cartridge 24 can be configured to contain about 3 mL of PTH. In an embodiment, cartridge has a diameter of about 12 mm and a height of approximately 64 mm to contain 3 mL of medicament, although other dimensions can be used to achieve the desired accuracy. Cartridges containing more or less medicament can be provided and can vary in diameter, height or both. For example a cartridge can be configured to hold between about 1 mL and 10 mL of liquid medicament, and more preferably between about 2 mL and 5 mL of liquid medicament. Similarly, the device can be configured to dispense different amounts of the liquid medicament per dose. For example, a dose of liquid medicament can be between about 0.05 mL and 0.2 mL. Preferably a dose of liquid medicament is between about 0.07 mL and 0.1 mL. Further, the overall volume can be increased to include a predetermined amount of additional volume that remains in the cartridge when the intended dosing is complete. This reduces the likelihood of an incomplete final dose or the presence of air in an injection.

In an embodiment, a given lower housing 24 can be used to hold a number of differently-sized cartridges, such as by providing a cartridge sleeve that is sized to act as a shim between the lower housing 22 and a cartridge that is smaller than the interior of lower housing 22. A number of differently-sized cartridge sleeves can be provided, as necessary for differently-sized cartridges. Additionally, larger and smaller variations of a cartridge can be formed having the same diameter but with different heights and correspondingly-sized lower housing units, all of which can be used with a single sized proximal section 30.

Cartridge 24 has a dispensing end 26 that is configured for providing an outlet for the administered dose of the liquid medicament. Suitable dispensing ends are known and are preferably in the form of a needle of a length and configuration to deliver the medicament to the desired depth and injection site. Alternatively, the dispensing end can be configured to be attached to an intravenous line or the like. In the embodiment of FIG. 1, dispensing end 26 is fitted with a needle 28 extending therefrom. Needle 28 can be fitted with a protective cover 21 thereover to protect those handling or who may otherwise encounter injector 10. Cartridge 24 further has a lumen with a side 23 that is closed and sealed with a plunger 25 that is slideably fitted within the interior of cartridge 24 lumen. Plunger 25 is further configured to seal open end 23 to prevent leakage or contamination of the liquid medicament. The distal face of plunger 25 generally defines the height and thereby the volume of the interior of the cartridge 24. By advancing plunger 25 toward the dispensing end 26, the volume of the cartridge 24 is decreased, and an amount of the liquid medicament is expelled from the dispensing end 26 that corresponds to the reduction in volume caused by the movement of the plunger. In the exemplary embodiment of cartridge 24 discussed above, the desired predetermined dose of 0.08 mL is dispensed by movement of plunger 25 through a distance of about 1.1 mm.

Proximal section 30 contains a dosing mechanism that is contained within upper housing 32 and configured to cause movement of plunger 25 through the predetermined dosing distance in a number of successive increments that corresponds to the number of doses to be administered. The dosing mechanism includes a user-manipulable trigger that allows the user to actuate the mechanism. In the embodiment shown in FIGS. 1 and 2, the trigger is shown in the form of a push button 34 that is moveable within upper housing 32 in a direction along the proximal-distal axis 14 direction and to be rotatable about axis 14. Such motion is preferably constrained, as will be discussed below. The dosing mechanism further includes a plunger rod 36 having a washer 18 affixed to the distal end thereof that is configured to contact the proximal end of plunger 25 and to exert a force thereon to cause movement of the plunger 25. Plunger rod 36 includes a plurality of threads along the outside surface thereof which engage the threaded interior of nut 60 such that turning of plunger rod 36 causes advancement thereof through nut 60. The dosing mechanism further includes driver 38 that is disposed within upper housing 32 so as to be rotatable about the proximal-distal axis 14. The driver 38 is preferably fixed longitudinally to prohibit translational movement along the proximal-distal axis 14 with respect to the housing 32. Both driver 38 and upper housing 32 can be formed of at least two separate parts that can be affixed, preferably by snap-fit, to each other. The preferred head 37 of plunger rod 36 is rotationally constrained within the driver 38, and in the embodiment shown, fits within and engages the internal profile of driver 38 such that rotation of driver 38 causes rotation of plunger rod 36. Head 37 is preferably longitudinally slideable within driver along axis 14.

Figure 3:
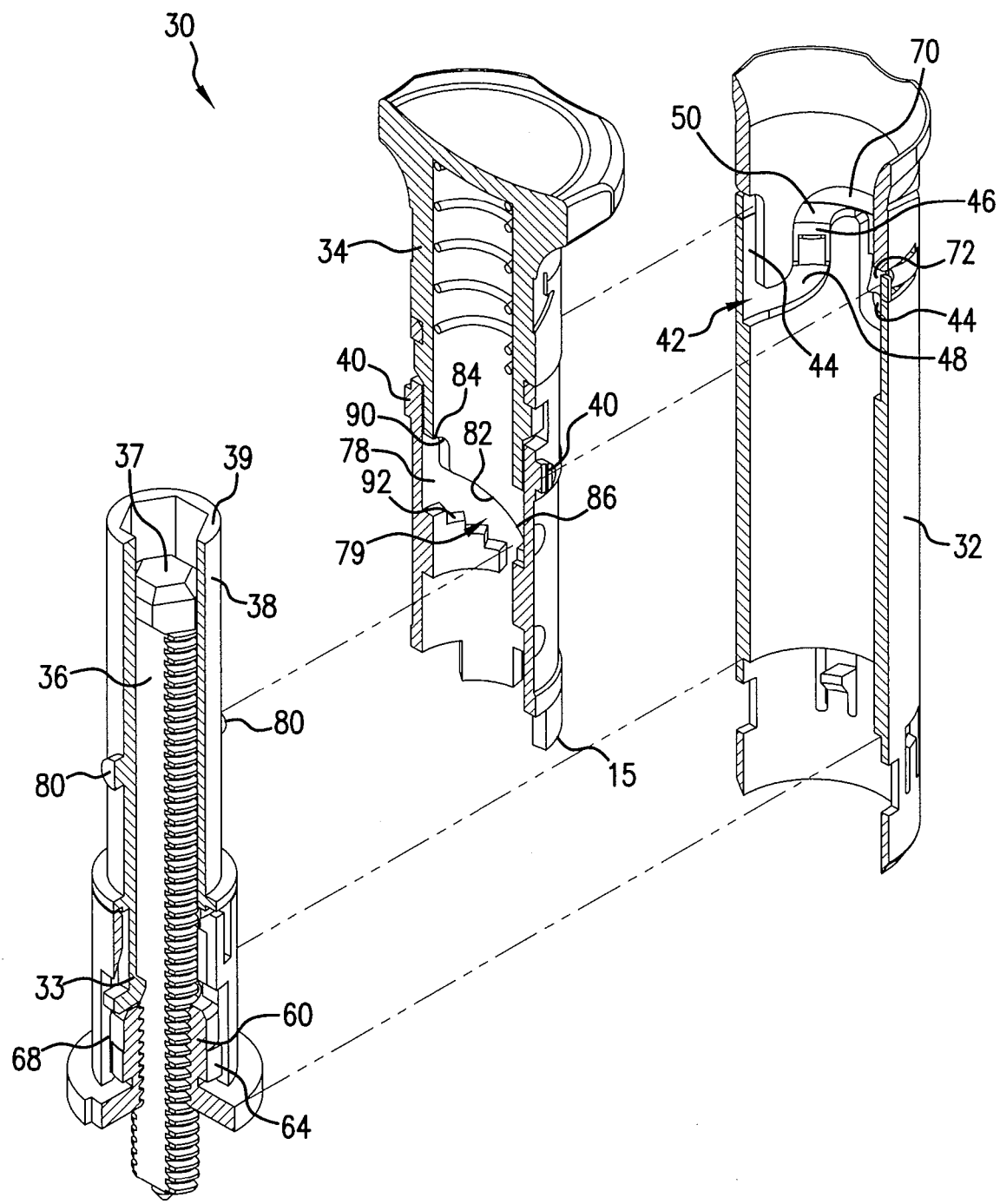
FIG. 3 is an exploded, cross section view of the proximal portion of the injection device of FIG. 1.

FIG. 3 shows the dosing mechanism including driver 38, push button 34 and upper housing unit 32. To produce the desired dosing of the liquid medicament, the dosing mechanism is configured to produce a substantially equal incremental movement based on repetitive movements of push button 34. Preferably, the dosing mechanism is configured to administer fixed doses of the liquid medicament by repetitive movements of push button 34 of an equal amount. The motion of push button 34 is constrained such that it is only moveable in a predetermined, cyclical/repeating pattern. This can be accomplished by forming a set of projections 40 on the outside surface of push button 34 and by forming an upper track 42 on the interior surface of upper housing unit 32. Projections 40 fit within upper track 42 and both are sized so that the projections are slideable within upper track 42 but are securely held such that the sliding movement has minimized play. Alternative arrangements are possible for use in the dosing mechanism and can include the formation of projections on the interior surface of upper housing 32 with corresponding tracks formed on the exterior of push button 34. Additional alternative structures can replace the projections and tracks described herein to carry out similar functions. Upper track 42 can have a number of repeating sections that can be identical to each other, or can have a single section. Each section includes a dispensing portion 44 and a resetting portion 46. Dispensing portion 44 extends generally longitudinally, and is preferably oriented to extend in a substantially straight line substantially parallel to proximal-distal axis 14 of injector 10. When projections 40 are positioned within dispensing section 44, the movement of push button 34 is restricted to movement along the track, which in the preferred embodiment is non-rotating movement in the proximal-distal direction and the amount of movement is equal to the difference between the length of dispensing section 44 and the height or diameter of the projection 40.

As shown in FIG. 4A, resetting portion 46 is preferably generally "S"-shaped. Preferably, it has a lower horizontal portion 48, an upper horizontal portion 50, a substantially vertical portion 52 disposed between the horizontal portions 48,50 and two curved portions 54,56 that link respective ones of the upper and lower horizontal portions 48,50 to the substantially vertical portion 52. Preferably, upper track 42 includes a plurality of dispensing portions 44. Further preferably, upper track 42 includes a plurality of resetting portions 46 arranged such that a resetting portion links the distal end of a dispensing portion to the proximal end of a dispensing portion, which, in embodiments with repeated sections, is the adjacent dispensing portion. In such an arrangement, alternating, successive dispensing portions and resetting portions form a cyclic and preferably repeating pattern within the interior surface of upper housing 32 such that the movement of push button 34 is constrained in motion within the pattern.

In the embodiment of FIG. 3, upper track 42 includes four dispensing portions 44 and four resetting portions 46. While the number of resetting portions 46 must always be equal to the number of dispensing sections, the total number of dispensing and resetting portions can vary. In general, the number of dispensing and resetting sections can be selected to give the desired, preferably fixed, dose size, which corresponds to the geometry of other features of the dosing mechanism that will be explained below. The number of dispensing and resetting sections can be limited by the size and configuration of upper housing 32.

The pattern of linked dispensing and resetting portions 44,46 preferably restricts the movement of the push button 34 to a dispensing motion and a resetting motion. The dispensing motion involves movement of the push button 34 in a distal direction from a ready position to an end position. In the ready position, the plunger is located preferably such that the projections 40 are positioned at the proximal end of the dispensing portions 44. In the end position the projections 40 are positioned at the distal end of the dispensing portions 44. It is noted that the number of projections 40 located on push button 34 can vary. In the embodiment shown, wherein the housing has a upper track 42 including four sets of linked dispensing 44 and resetting 46 portions, push button 34 can have between 1 and 4 projections, most preferably having one projection per the number of repetitions of the linked dispensing 44 and resetting 46 portions of upper track 42. Multiple projections can be used to provide a more robust structure with more accurate movement. In an embodiment having multiple projections, the projections are preferably located along a common radial plane and are spaced apart at intervals equal to the interval of the dispensing and resetting portions 44,46. For example, in the embodiment, shown in FIG. 4, four projections can be used and spaced apart at 90° intervals.

The resetting motion of push button 34 includes a combination of rotation of push button 34 and translational movement of push button 34. The specific movement includes rotational movement such that the projections 40 first move generally circumferentially or horizontally from the distal ends of dispensing portions 44 through the lower horizontal portions 48 thereof and translational movement in the proximal direction such that projections 40 move through generally axial or vertical sections 52 thereof and, finally, rotational movement such that projections 40 move through upper generally circumferential or horizontal sections 50 thereof to the proximal ends of the dispensing portions 44. After movement through the resetting portion has been completed, push button will have been rotated through an angle equal to the phase of the dispensing and resetting sections 44,46. In the embodiment shown, such an angle will be approximately 90°. Other arrangements resulting in different angles are possible. After such rotation, the projections 40 will be positioned within a dispensing section 44 that is adjacent to the one in which they were located prior to the resetting motion. It is noted that when the projections 40 move through the curved sections 54,56, the motion will include both rotational and vertical movement.

Figure 2:
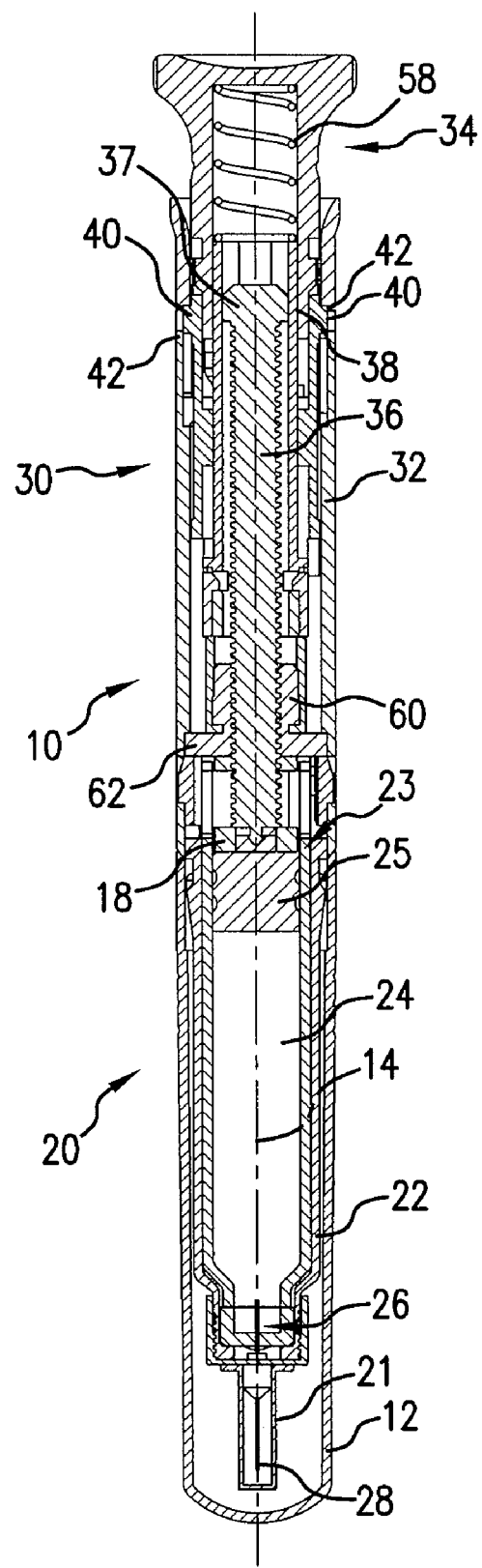
FIG. 2 is a cross-sectional view of the injection device of FIG. 1.

To aid a user of injector 10 in carrying out the resetting motion, spring 58 is included within upper push button 34. As shown in FIG. 2, the preferred spring 58 is disposed between the upper surface 39 of the driver 38 and the upper surface of the cylindrical recess in the push button 34. Spring 58 is arranged such that when push button 34 is depressed through the dispensing motion, spring 58 is compressed. Alternatively, spring 58 can be disposed between the upper surface of flange 62 formed in nut 60 and the lower edge 15 of push button 34 in the upper housing 32. When push button 34 is rotated in the initial stage of the resetting motion it preferably remains compressed until the projections enter the curved portion of the resetting section 46. At this point, spring 58 will begin to decompress and will urge push button 34 in the proximal direction. The decompression of spring 58 will aid the user in the movement of the push button in the proximal direction and can further be configured to carry out motion in the proximal direction by itself, with no proximally-directed force required of the user. Once movement in the proximal direction is completed, including movement of projections through the vertical portion and both curved portions of resetting section 46, resetting is completed by rotation through the upper horizontal portion of resetting section 46. Preferably, resetting portion 46 is shaped such that the decompressive force from spring 58 contributes to a smooth motion of push button 34 during resetting. Preferably, this smooth motion is such that the user only exerts a torsional force on push button to cause rotation thereof, a majority of the proximal translational movement being accomplished by spring 58, but with the user still required to actively move the push button 34 to initiate and/or complete the resetting, preferably to prevent fully automated and possibly undesired resetting.

Upper track 42 preferably includes anti-retrograde features that help to restrict the motion of push button to a forward direction, and to prevent retrograde movement thereof along upper track 42. In the present embodiment, the desired directions are translation in the distal direction for dispensing, and rotation in the clockwise direction and translation in the proximal direction during resetting. Further the anti-retrograde features are configured such that at the end of the dispensing motion, push button 34 can only be moved in the resetting direction, and such that at the end of the resetting motion, push button 34 can only be moved in the dispensing projection.

As shown in FIG. 3, the anti-retrograde features of upper track 42 include a series of tabs extending into the track, preferably from the upper housing 32. The tabs are preferably angled such that projections 40 can pass thereover in one direction, but are prevented from moving thereover in the opposite direction. The series of tabs preferably includes a plurality of post-reset tabs 70, preferably oriented horizontally within and at the end of the upper horizontal sections 50 of resetting portions 46, and a plurality of post-injection tabs 72 preferably oriented vertically and at the end of the dispensing portions 44. The free ends of horizontal tabs 70 are preferably positioned at the intersection of resetting portions 46 and the proximal ends of the dispensing portions 44 such that the movement of projections 44 through the upper section 50 includes movement over the post-reset tabs 70 and such that when projections move into the dispensing sections 44 the ends of the post-reset tabs 70 abut projections 40. Further, post-reset tabs 70 are oriented such that the movement of push button in the resetting direction is such that projections 40 deflect post-reset tabs 70 to move thereover. The free ends of post-reset tabs 70 are preferably concave in shape such that projections 40 nest therein when push button 34 is in the ready position. This arrangement can provide an audible and tactile feedback for the user when push button 34 is depressed in the dispensing motion, causing projections 40 to move out of the nested relationship with free ends of post-reset tabs 70, which can cause slight deflection of post-reset tabs 70. In an alternative embodiment, post-reset tabs can be positioned within resetting portions 46 at a location near the middle thereof, to prevent reverse movement of the pushbutton during resetting along a midpoint thereof.

Post-injection tabs 72 are configured such that the ends thereof abut projections 40 when projections 40 are positioned at the distal end of dispensing sections 44. Post-injection tabs 72 are further oriented such that movement of push button 34 in the dispensing direction is such that projections 40 deflect post-injection tabs 72.

As stated previously, the dosing motion of push button 34 are preferably intended to cause a predetermined, fixed dose of liquid medicament to be dispensed from cartridge 24. Accordingly, the dispensing mechanism is structured to transfer the linear motion of push button 34 through the dispensing movement to rotation of plunger rod 36 through an angle necessary to move plunger 25 through the distance corresponding to one dose. As discussed above, driver 38 is structured such that rotation of driver 38 causes rotation of plunger rod 36 while permitting plunger rod 36 to translate axially with respect thereto. Push button 34 and driver 38 are, accordingly, structured to have interrelating features that cause rotation of driver 38 with response to the dispensing motion of push button 34.

As shown in FIG. 3, push button 34 forms a hollow cavity therein that is sized such that driver 38 can fit at least partially therein. The interior surface of push button 34 includes a recess 78 that has a depth sufficient to receive projections 80 formed on the outside surface of driver 38. Recess 78 extends around preferably the entire interior surface of push button 34 to provide a path through which driver projections 80 can pass as driver 38 is turned within push button 34. Additionally recess 78 includes a pair of inclined cam surfaces 82 that face the distal end of injector 10 and include a top end 84 and a bottom end 86. Surfaces 82 are positioned such that when push button 34 is in the ready position, each bottom end 86 is positioned so as to be aligned axially over the respective projection 80, preferably spaced slightly proximally thereof. This arrangement is illustrated in FIGS. 4A and 4B, in which FIG. 4A shows the exterior of injector 10 with the internal features, including upper track 42, surface 82, and both sets of projections 40,80, shown in hidden lines. Further, FIG. 4B shows upper track 42 and recess 78 in a single, planar view, as if the interior surfaces of upper housing 32 and push button 34 were flattened. Arrow 2 shown in FIG. 4A shows the general direction of rotational motion for push button 34, arrow 3 shows the direction and general path through which projection 44c moves in response to the movement of push button 34, which is further discussed herein, and arrow 4 shows the general rotational direction of recess 78, caused by corresponding movement of pushbutton 34, including rotation in the direction of arrow 2. In the initial, ready position depicted in FIGS. 4A and 4B, each one of the projections 40a,40b,40c,40d is positioned at the proximal end of its respective dispensing section 44a,44b,44c,44d and is prevented from passing back into the adjacent resetting section 46d,46a,46b,46c by a horizontal tab 70.

As shown in FIGS. 6A and 6B, when push button 34 is depressed so as to move distally to a fired, or post-injection state, projection 40a slides distally from the proximal end to the distal end of dispensing portion 44a. Other projections 40b,40c,40d move similarly within respective dispensing portions 44b,44c,44d. As previously discussed, projections 40a,40b,40c,40d move over and deflect post-injection tabs 72 such that when push button 34 reaches the end of the dispensing motion, it is prevented from being forced backwards therefrom. The movement of push button 34 in the distal direction also causes inclined surfaces 82a,82b to move distally, as they are formed within push button 34. Because driver 38, and thus projections 80a,80b are preferably in a fixed axial position with respect to the housing, but are rotatable about axis 14 of the device, the movement of inclined surfaces 82a,82b in the distal direction causes projections 80a,80b to rotate along plane 88, following respective surfaces 82a,82b and causing driver 38 to rotate. Preferably, this motion causes driver 38 to rotate through an angle of about 90° in one dispensing motion, with the inclined surfaces 82a,82b having a horizontal length sufficient to provide such rotation through the distance through which push button 34 is configured to travel. It is noted that this distance can determine the selected angle of inclined surfaces 82a,82b and can, accordingly be configured to provide a desired amount of mechanical advantage in turning driver 38.

Preferably, the distance of travel for push button 34 is determined such that, relative to the horizontal length of surface 82, which is influenced by the overall size of injector 10, surface 82 forms an angle 89 (FIG. 5) relative to line 87 that extends axially in the direction of motion of push button 34 during the dosing motion. Preferably, angle 89 is between 40° and 70°. In a preferred embodiment, angle 89 is between 55° and 60°, and more preferably about 56°. Angle 89 is preferably optimized to prevent unintended additional dispensing of the liquid medicament during or immediately after dosing due to compression and subsequent re-expansion of plunger 25. The rotational motion of projections 80a,80b and driver 38 stop when projections 80a,80b pass respective top edges 84a,84b of inclined surfaces 82a,82b and come to rest along the top portions 90a,90b of recess 78. Preferably, top edges 84a,84b of inclined surfaces 82a,82b meet top portions 90a,90b of recess 78 so as to form a corner therebetween to produce a tactile effect that is distinguishable by the user of injector 10 to give feedback to the user of dose completion. The movement of projections 80a,80b over the corner can also produce tactile and/or auditory feedback.

The dosing mechanism includes an additional anti-retrograde feature between push button 34 and upper housing 32 to prevent movement of push button 34 in the proximal direction once dosing has begun in order to protect the accuracy of the dosing and preventing aspiration into the cartridge 24. As shown in FIG. 5, recess 78 forms a pair of stepped surfaces 92a,92b that are each disposed oppositely from a respective inclined surface 82a,82b. Stepped surfaces 92a,92b are generally oriented such that the horizontal surfaces thereof face the proximal direction. Projections 80a,80b each include an indentation 94a,94b that is shaped to receive an individual step therein. As shown in FIG. 5, this arrangement is such that once the dosing motion of push button 34 has been initiated, a subsequent movement of push button 34 in the proximal direction before the end of the dosing motion has been reached, will cause the indentations 94a,94b of projections 80a,80b to engage one of the individual steps formed in a respective stepped surface 92a,92b, which will prevent any further proximal motion of push button 34. It is noted that because push button 34 is prevented from rotating while in the dispensing motion by the upper track 42, indentations 94a,94b cannot be disengaged from surfaces 92a,92b except by further movement of push button 34 in the distal direction. A lower track 79 is formed between the upper and lower surfaces, in which projections 80 are confined in movement. It is noted that the reference to "upper" and "lower" tracks refers only to an exemplary embodiment in which upper track 42 is positioned above, or proximally, of lower track 79. Other embodiments are possible, however, in which lower track 79 is positioned proximally of upper track 42. Additional arrangements are possible to achieve the desired motion of driver 38 upon movement of push button 34 in the dispensing direction, including forming projections on the inside surface of push button 34 and a corresponding track on the exterior surface of driver 38.

FIGS. 7A and 7B show the relative position of the elements of the dispensing mechanism at a midpoint along the resetting motion of push button 34. During the resetting motion, projections 80a,80b are not influenced by the geometry of recess 78. Accordingly, projections 80a,80b and, thus, driver 38 remain stationary during the resetting motion of push button 34. The shape of the portion of recess 78 that is between each pair of inclined surfaces 82a,82b and stepped surfaces 92a,92b is such that it does not cause projection 80 to interfere with the resetting motion of push button 34 as projection 40 moves through resetting portion, as described above so that no rotation of the driver is caused during resetting. In the position shown, projections 40a,40b,40c,40d have moved over tabs 71, which thereby prevent any backwards movement of projections 40a,40b,40c,40d thereover. This prevents push button 34 from being depressed during the resetting motion and further prevents push button from being fully depressed before the resetting motion has been completed.

Figure 9:
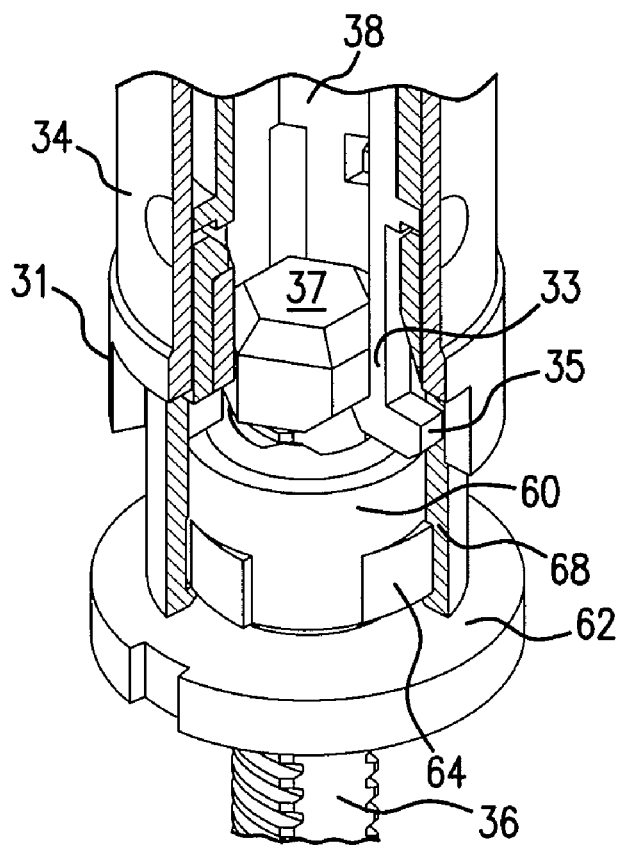
FIG. 9 is a cut-away view of the lockout mechanism of FIG. 8.

As shown in FIG. 9, to prevent driver 38 from rotating backwards due to friction with push button 34 while push button 34 is being moved through the resetting motion, nut 60 is formed with a plurality of ramps 64. Ramps 64 are preferably arranged to allow movement of driver 38 in the desired dosing direction (which is counter-clockwise in the embodiment described herein), but to engage recesses 68 in driver 38 after the dosing step is completed to prevent driver 38 from being rotated in a direction opposite the dosing direction.

As shown in FIGS. 7A and 7B, once the resetting motion of push button 34 has been completed, projection 40a is located in at the proximal end of dispensing section 44b of upper track 42. Further, bottom edge 86b of surface 82b is positioned just proximal of and is rotationally aligned with projection 80a of driver 32. As such, the counterclockwise rotation of driver through an angle of 90° that results from the dispensing motion of push button 34 and the clockwise rotation of push button 34 through an angle of 90° that is carried out as part of the resetting motion results in an aggregate movement between push button 34 and driver 38 of approximately 180° for each cycle of dosing and subsequent resetting. Accordingly, after a subsequent dosing and resetting of push button 34, bottom edge 86a will again be aligned with projection 80a, at which time projection 40a will be positioned within dosing section 44c. After the next steps of dosing and resetting, bottom edge 86b will again be aligned with projection 80a and projection 40a will be positioned within dosing section 44d. After another dosing and resetting, the system will be in the original position illustrated in FIGS. 4A and 4B.

Additional arrangements for the dosing mechanism are possible that include a different number of inclined surfaces within the push button and a different number of corresponding pairs of dispensing and resetting sections within the track. As discussed above, the rotation of the driver and the push button in opposite directions means that the number of dosing and resetting cycles carried out in a full rotation of the push button will preferably be the same as the number of dosing and resetting cycles carried out in a full rotation of the driver. Accordingly, the dosing mechanism will include twice as many pairs of dispensing and resetting sections within the track as the number of inclined surfaces within the recess. Therefore, a dosing mechanism can be formed with a single inclined surface and two sets of dosing and resetting sections, in which the driver will rotate through an angle of about 180° for each dosing motion of push button, after which the push button will be rotated through about 180° during resetting. Further, a dosing mechanism can be formed with three inclined surfaces and six sets of dosing and resetting sections, in which the driver will rotate through an angle of about 60° for each dosing motion of the push button, after which the push button will be rotated through about 60° during resetting. Additional inclined portions can be added, reducing the rotation of the driver and increasing the number of dispensing and resetting sections accordingly.

Such a variation in the number of inclined portions can be used to vary the dose size. That is, given a similarly shaped cartridge and plunger rod thread pitch, a decrease in the number of inclined portions will increase the amount of rotation for a single dose, thus increasing the dose size. Similarly, increasing the number of inclined portions will decrease the amount of rotation for a single dose, which will decrease the dose size.

The dose size can also be varied by the geometry of the threads formed on plunger rod 36 and nut 60. That is, by increasing the pitch of the threads, the linear distance traveled by plunger rod, and therefore plunger 25 is increased, leading to a greater dose size. Conversely, by decreasing the pitch of the thread, the dose size is reduced. The dose size can also be varied by changing the diameter of cartridge 24. A higher diameter will increase the dose size, while a smaller diameter will decrease the dose size. These factors can be adjusted to derive an injector that contains a desired amount of liquid medicament and will produce the desired number of doses at a desired, preferably fixed, amount, and will have the desired dosing and resetting motions.

Figure 8:
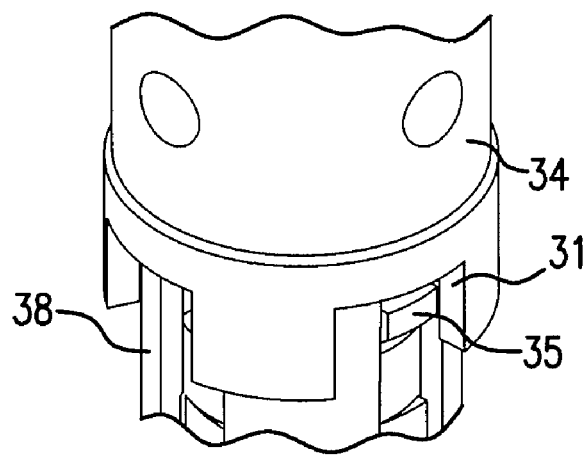
FIG. 8 is a perspective view of a lockout mechanism used in the injection device of FIG. 1.

FIGS. 8 and 9 show a final lockout mechanism that is included in injector 10 and disables injector from further motion of the dosing mechanism once the final dose has been administered. Once the final dose has been administered head 37 of plunger rod 36 moves to a position such that it is adjacent the proximal surface of nut 60. Driver 38 includes at least one arm 33 that is resiliently flexible and structured to extend outwardly when head 37 of plunger rod 36 is adjacent the proximal surface of nut. When head 37 forces arm 33 outwardly, foot 35, which is affixed to the distal end thereof, extends outwardly into notch 31 formed in the bottom edge of push button 34. The extension of foot 35 into notch 31 prevents push button 34 from being rotated. Because the anti-retrograde features of the dosing mechanism prevent proximal movement of push button 34, no movement of push button 34 is possible. This disables injector 10, preventing accidental or intentional further use.

Upper housing 32 can further include a window 100 through which visual indicia relating to the position and intended movement the dosing system are visible. Such indicia are preferably formed on the outside surface of push button 34 and are positioned to be visible at various instances during the dosing and resetting cycle. As shown in FIG. 4A, a first indicia 102, which is shown as a circle but can include other shapes and can incorporate a color, such as green, to add to the affect thereof, is positioned within window 100 when push button 34 is in the ready position to indicate that the dosing mechanism is ready for dosing. As shown in FIG. 6A, a second indicia 104, which is shown as a circle but can include other shapes and can incorporate a color, such as red, to add to the affect thereof, is positioned within window 100 after the dosing movement of push button 34 has been completed to indicate that dosing is complete. Alternatively, a horizontal arrow directing the user to turn push button 34 to complete resetting of the dosing mechanism can replace second indicia 104. A third indicia could be positioned on push button 34 to pass through window 100 during resetting to signal to the user that the resetting motion has not yet been completed. Upper housing 32 can also include a series of notches 112 disposed along the edge thereof, and push button 34 can include a series of arrows 110 that align with the notches when push button 34 is in the ready position. This can help a user of injector 10 in knowing when the resetting motion has been completed.

While the dosing mechanism described herein is shown as a part of a needled injection device for a liquid medicament, it is understood that the mechanism can be used in other dispensing devices that include a dispenser that is actuated by linear motion. This includes injection devices that use a mechanism other than a push button as well as other dispensing devices for gels or the like which may or may not contain a medicament.

All of the references specifically identified in the detailed description section of the present application are expressly incorporated herein in their entirety by reference thereto. The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments may be devised by those skilled in the art. For example, the features for the various embodiments can be used in other embodiments. In an alternative embodiment, the housing can be fixed to the bracket, and the inner portion, defining at least the bottom of the chutes can slide in and out of the housing. Therefore, it will be understood that the appended claims are intended to cover all such modifications and embodiments that come within the spirit and scope of the present invention.

What is claimed is:

1. A medicament dispensing mechanism configured to eject successive doses of the medicament from a medicament chamber, comprising:
   a housing;
   a plunger rod configured for ejecting the doses of medicament from the chamber; and
   an actuation mechanism that comprises a trigger associated with the housing and having a ready position and a fired position with respect thereto, the trigger being configured for manipulation by a user for successive movement in:
      a dosing motion from the ready position to the fired position generally in axial translation in which the trigger is associated with the plunger rod to cause the plunger rod to eject one of the doses of a predetermined volume, and
      a resetting motion from the fired position to the ready position that comprises axial rotation, wherein the trigger is uncoupled from the plunger rod during the resetting motion; and
   an anti-retrograde mechanism associated with the actuation mechanism and configured to prevent movement of the actuation member in a direction opposite to an operational direction associated with each of the dosing motion and the resetting motion;
   wherein the anti-retrograde mechanism prevents the actuation mechanism from returning to the ready position associated with the dosing motion from the fired position associated with the dosing motion.

2. The dispensing mechanism of claim 1, wherein the trigger comprises a plurality of ready positions and fired positions disposed in sequence with each other, and wherein the ready positions are circumferentially spaced about the housing.

3. The dispensing mechanism of claim 1, wherein the anti-retrograde mechanism prevents movement of the actuation mechanism in a direction opposite the operational direction associated with each of the dosing motion and the resetting motion through at least a portion of the dosing motion and resetting motion.

4. The dispensing mechanism of claim 3, wherein the anti-retrograde mechanism is associated with the trigger for preventing rearward movement thereof from the ready position against the direction of the resetting motion, and wherein the anti-retrograde mechanism is associated with the trigger for preventing rearward movement thereof from the fired position against the direction of the dosing motion.

5. The dispensing mechanism of claim 4, wherein:
   one of the trigger and housing includes a projection; and
   the other of the trigger and housing includes a track for receiving the projection and defining the dosing and resetting motions, wherein the track has a first tab disposed therein with a free end configured for engaging the projection and preventing rearward movement thereof from the fired position against the direction of the dosing motion, and wherein the track has a second tab disposed therein with a free end configured for engaging the projection and for preventing rearward movement thereof from the ready position against the direction of the resetting motion.

6. The dispensing mechanism of claim 1, wherein the actuation mechanism comprises a driver rotatably associated with the housing and driven to rotate in a driving direction by the trigger during the dosing motion.

7. The dispensing mechanism of claim 6, wherein the driving direction is in an opposite rotational direction than the rotational spacing between the fired position and adjacent ready position of the trigger, the driver being associated with the plunger rod for causing the plunger rod to eject said one of the doses.

8. The dispensing mechanism of claim 6, wherein:
   one of the housing and trigger includes a first projection, and the other of the trigger and housing includes a first track, wherein the first track is configured for receiving the first projection and defines the dosing and resetting motions of the trigger with respect to the housing; and
   one of the trigger and driver includes a second projection, and the other of the trigger and driver includes a second track, wherein the second track is configured for receiving the second projection, applying a force to the second projection during the dosing motion of the trigger to rotate the driver in the driving direction, and allowing the resetting motion of the trigger without rotating the driver.

9. The dispensing mechanism of claim 8, wherein the housing defines the first track and the trigger defines the first projection, and wherein the trigger defines the second track and the driver defines the second projection, wherein the first track defines a succession of a plurality of the ready positions interposed in continuous series by a plurality of the fired positions and paths for the corresponding dosing and resetting motions therebetween, and wherein the second track comprises a plurality of driving portions for causing the trigger to rotate the driver in each of the dosing motions connected in continuous series by alternately applying a force to the second projection during successive dosing motions of the trigger to rotate the driver in the driving direction.

10. The dispensing mechanism of claim 8, wherein the second track has a resetting portion aligned substantially axially to allow the resetting motion of the trigger without rotating the driver.

11. The dispensing mechanism of claim 6, wherein the driving direction is opposite from the direction of rotation of the trigger in the resetting motion.

12. The dispensing mechanism of claim 1, wherein the predetermined volume includes a fixed volume.

13. The dispensing mechanism of claim 1, wherein the anti-retrograde mechanism includes a track and at least one tab.

14. The dispensing mechanism of claim 1, wherein the operational direction associated with the dosing motion includes a distal translation and the operational direction associated with the resetting motion includes a rotation and a proximal translation.

15. The dispensing mechanism of claim 1, wherein the medicament is a parathyroid hormone.

16. An injector, comprising:
    the dispensing mechanism of claim 1;
    a cartridge associated with the housing and defining the chamber;
    a plunger disposed in the chamber to seal the medicament therein, wherein the plunger rod is associated with the plunger for forcing the plunger in a distal direction for ejecting the doses; and
    a needle in fluid communication with the chamber for injecting the doses into a patient.

17. A medicament dispensing mechanism configured to eject successive doses of the medicament from a medicament chamber, comprising:
    a housing;
    a plunger rod configured for ejecting the doses of medicament from the chamber;

an actuation mechanism that comprises a trigger associated with the housing and having a ready and a fired position with respect thereto, the trigger being configured for manipulation by a user for successive movement in:
- a dosing motion from the ready position to the fired position, during the dosing motion the trigger being associated with the plunger rod to cause the plunger rod to eject one of the doses; and
- a resetting motion from the fired position to the ready position, wherein the trigger is uncoupled from the plunger rod during the resetting motion; and an anti-retrograde mechanism associated with the actuation mechanism for preventing movement thereof against the direction of operation of the actuation mechanism through at least a portion of the dosing motion and the resetting motion;

wherein the anti-retrograde mechanism prevents the actuation mechanism from returning to the ready position associated with the dosing motion from the fired position associated with the dosing motion.

18. The dispensing mechanism of claim 17, wherein:

the actuation mechanism comprises a driver rotatably associated with the housing and driven to rotate by the trigger during the dosing motion;

the driver is associated with the plunger rod for causing the plunger rod to eject said one of the doses;

the anti-retrograde mechanism is configured for preventing rearward movement of the driver with respect to the trigger against the dosing motion;

one of the trigger and driver includes a projection; and the other of the trigger and driver includes stepped surfaces facing a relative path of the projection during the dosing motion, the stepped surfaces configured for engaging the projection during rearward movement therebetween for preventing rearward movement of the trigger.

19. The dispensing mechanism of claim 18, wherein the stepped surfaces are substantially flat and face axially, and wherein the projection defines a notch to receive an edge of the stepped surfaces.

20. The dispensing mechanism of claim 18, wherein said other one of the trigger and driver comprising a sloped surface opposite the stepped surfaces and engaged with the projection during the dosing motion to cause the trigger to cam the driver for rotating and driving the plunger rod.

21. The dispensing mechanism of claim 18, wherein the anti-retrograde mechanism is configured for preventing rearward movement of the driver with respect to the housing.

22. The dispensing mechanism of claim 18, wherein the anti-retrograde mechanism is configured for preventing rearward movement of the plunger rod.

23. The dispensing mechanism of claim 22, wherein the anti-retrograde mechanism is configured for preventing the rearward movement of the plunger rod only after a predetermined number of doses have been ejected from the chamber and disabling the actuation mechanism by including a flexible arm disposed within the housing, the plunger rod being configured to force a portion of the flexible arm axially outwardly after the predetermined number of doses have been ejected from the chamber, and the flexible arm being configured to engage a portion of the trigger to prevent further motion of the trigger in the resetting motion to disable the actuation mechanism.

* * * * *